(12) United States Patent
Cirotteau et al.

(10) Patent No.: US 7,306,611 B2
(45) Date of Patent: Dec. 11, 2007

(54) DEVICE FOR DELIVERING A BIOMATERIAL

(75) Inventors: Yves Cirotteau, Paris (FR); Eric Giangrande, Pontivy (FR)

(73) Assignee: Bio Holdings International Limited, Tortola (VG)

( * ) Notice: Subject to any disclaimer, the term of this patent is extended or adjusted under 35 U.S.C. 154(b) by 0 days.

(21) Appl. No.: 10/489,601

(22) PCT Filed: Sep. 18, 2002

(86) PCT No.: PCT/FR02/03185

§ 371 (c)(1),
(2), (4) Date: Mar. 18, 2004

(87) PCT Pub. No.: WO03/024369

PCT Pub. Date: Mar. 27, 2003

(65) Prior Publication Data

US 2004/0236340 A1    Nov. 25, 2004

(30) Foreign Application Priority Data

Sep. 19, 2001   (FR) ................... 01 12082

(51) Int. Cl.
*A61B 17/56*   (2006.01)

(52) U.S. Cl. ............... 606/92; 604/57; 604/164.01; 604/181; 222/387; 222/510

(58) Field of Classification Search ........... 606/92–94, 606/99; 604/21, 36, 38, 57–60, 164.01, 164.09, 604/164.1, 164.11, 174–75, 170.01, 170.02, 604/181, 187, 264, 285–88, 11, 13, 15; 222/286, 222/387, 510
See application file for complete search history.

(56) References Cited

U.S. PATENT DOCUMENTS 3,660,037 A * 5/1972 Sokol .................... 422/73

(Continued)

FOREIGN PATENT DOCUMENTS

DE          4022986          1/1992

(Continued)

*Primary Examiner*—Eduardo C. Robert
*Assistant Examiner*—Michael B Priddy
(74) *Attorney, Agent, or Firm*—Dennison, Schultz & MacDonald

(57) ABSTRACT

A device for delivering small spheres of biomaterial into a determined portion of a bone including a cylindrical hollow body of inside diameter D1 having a filling first end and a second end provided with a snap-fastener, a shutter-forming guide rod having a main portion that is cylindrical with an outside diameter D2 and presenting an enlarged cylindrical portion suitable for co-operating with the snap-fastener of the body, and a piston constituted by a cylindrical part presenting an outside diameter D3 and an axial bore of diameter D4. The diameter D3 is slightly smaller than the inside diameter D1 of the body and the inside diameter D4 is slightly greater than the diameter D2 of the rod in such a manner that, once the snap-fastener has been released, the rod can slide inside the piston, and the piston can slide inside the body.

5 Claims, 3 Drawing Sheets

U.S. PATENT DOCUMENTS

| | | | |
|---|---|---|---|
| 4,312,343 A * | 1/1982 | LeVeen et al. | 604/211 |
| 4,645,488 A * | 2/1987 | Matukas | 604/59 |
| 4,671,263 A | 6/1987 | Draenert | |
| 4,936,315 A * | 6/1990 | Lineback | 600/578 |
| 5,405,326 A * | 4/1995 | Haber et al. | 604/110 |
| 5,413,563 A * | 5/1995 | Basile et al. | 604/218 |
| 5,468,245 A * | 11/1995 | Vargas, III | 606/94 |
| 5,496,286 A * | 3/1996 | Stiehl et al. | 604/232 |
| 5,562,624 A * | 10/1996 | Righi et al. | 604/110 |
| 5,569,193 A * | 10/1996 | Hofstetter et al. | 604/89 |
| 5,681,279 A * | 10/1997 | Roper et al. | 604/57 |
| 5,860,946 A * | 1/1999 | Hofstatter | 604/15 |
| 5,951,526 A * | 9/1999 | Korisch et al. | 604/208 |
| 6,017,349 A * | 1/2000 | Heller et al. | 606/92 |
| 6,059,755 A * | 5/2000 | Michel | 604/207 |
| 6,090,080 A * | 7/2000 | Jost et al. | 604/207 |
| 6,319,233 B1 * | 11/2001 | Jansen et al. | 604/192 |
| 6,382,204 B1 * | 5/2002 | Jansen et al. | 128/200.19 |
| 6,425,920 B1 * | 7/2002 | Hamada | 623/17.16 |
| 6,582,438 B2 * | 6/2003 | DeMayo | 606/92 |
| 6,616,639 B2 * | 9/2003 | Gagnieux et al. | 604/192 |
| 6,673,049 B2 * | 1/2004 | Hommann et al. | 604/207 |
| 6,755,563 B2 * | 6/2004 | Wahlig et al. | 366/139 |
| 6,793,660 B2 * | 9/2004 | Kerr et al. | 606/93 |
| 7,033,343 B2 * | 4/2006 | McWethy et al. | 604/506 |
| 2002/0092871 A1 * | 7/2002 | Rickard et al. | 222/327 |
| 2003/0028151 A1 * | 2/2003 | Righi et al. | 604/218 |
| 2003/0075564 A1 * | 4/2003 | Wahlig et al. | 222/206 |

FOREIGN PATENT DOCUMENTS

EP          955022          11/1999

* cited by examiner

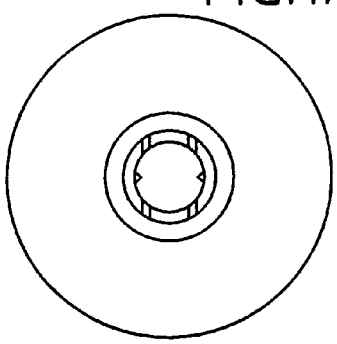
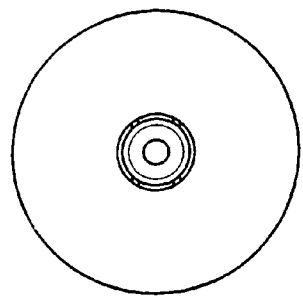
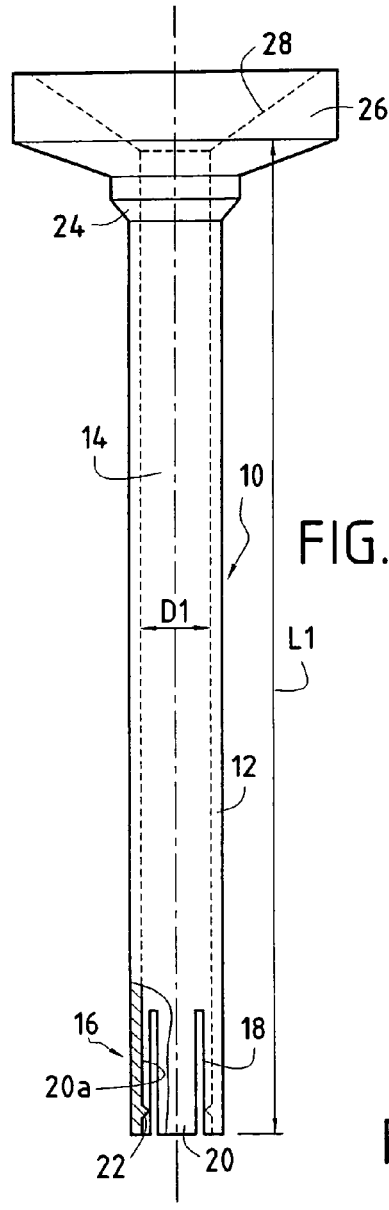
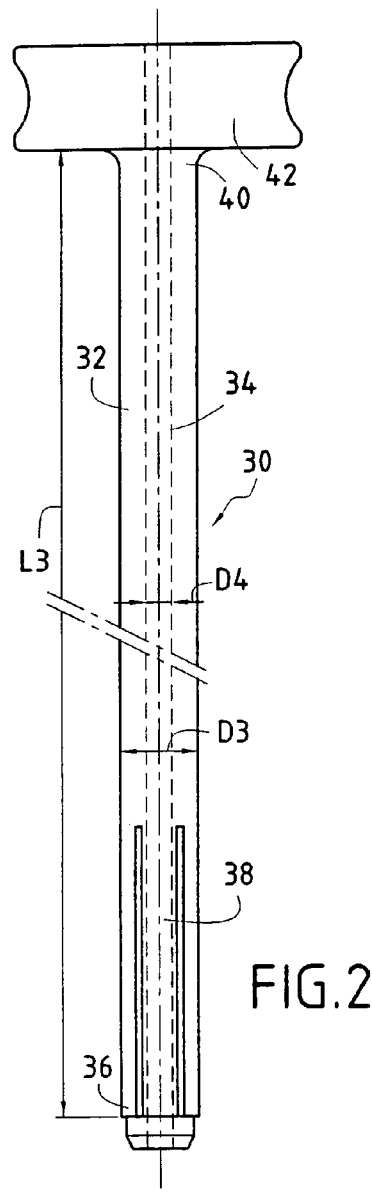
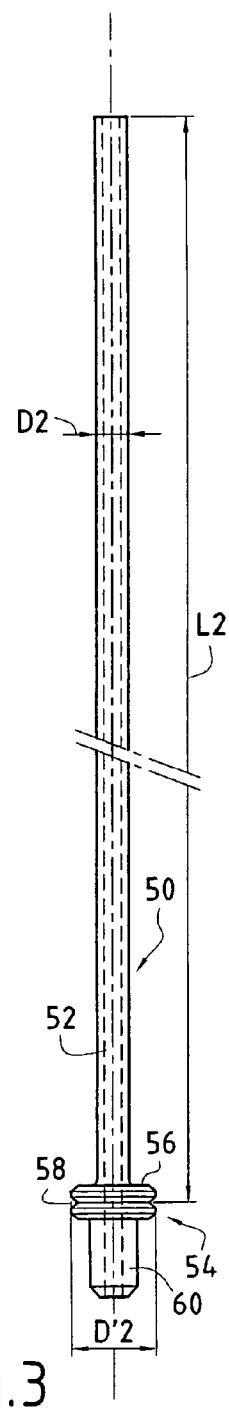

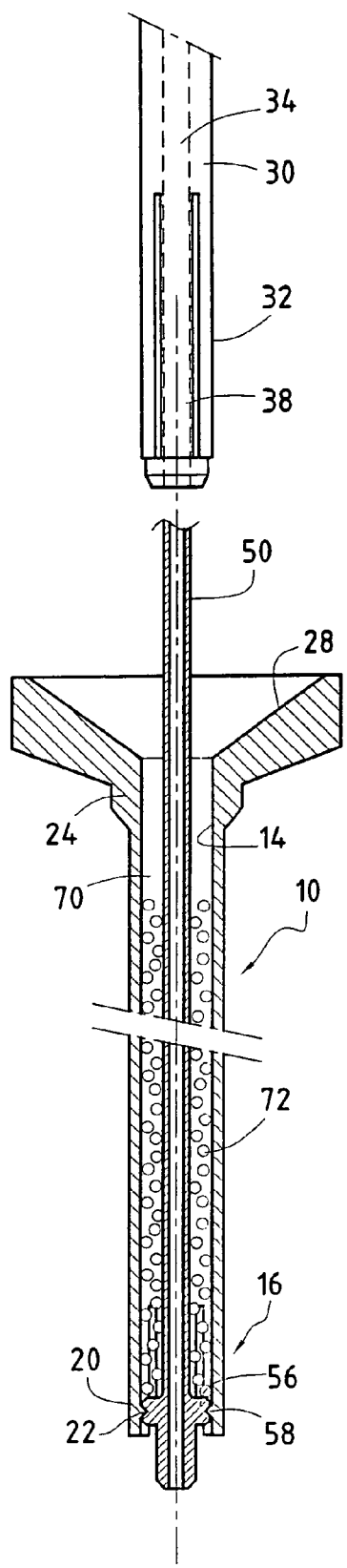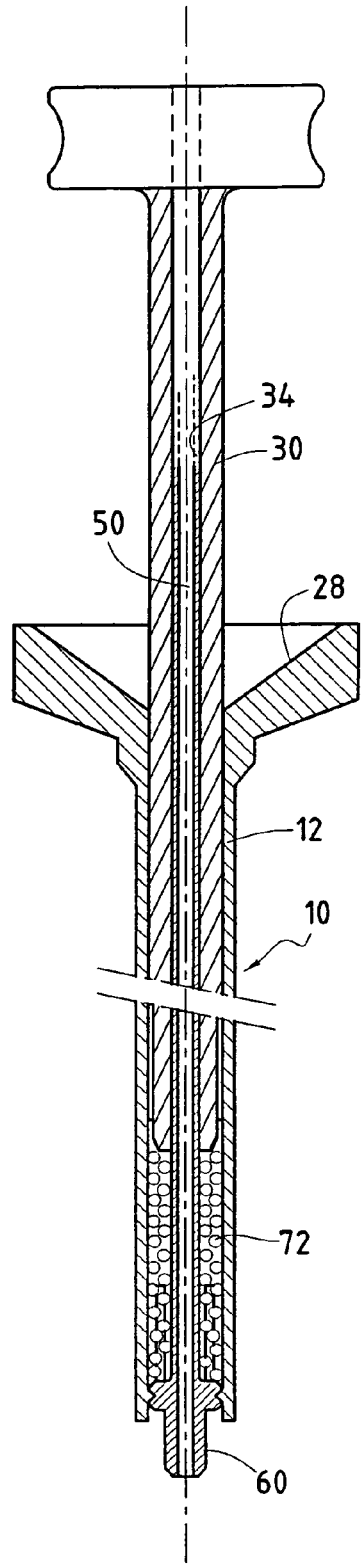

DEVICE FOR DELIVERING A BIOMATERIAL

This application is a filing under 35 USC 371 of PCT/FR02/03185, Sep. 18, 2002.

The present invention relates to a device for delivering small spheres of biomaterial into a determined portion of a bone.

In order to put into place certain implants or orthopedic structures such as a screw-and-plate system in a particular location of a bone, e.g. in the head of the femur (femoral metaphysis), it is necessary initially to use an auger to make a cavity that will subsequently be occupied by the implant or the orthopedic structure, i.e. the screw and the barrel of the plate, in the particular example under consideration. In order to ensure that the implant or the orthopedic structure is held in its cavity, it is necessary to insert a biomaterial into the cavity prior to introducing the screw or the implant, in order to stabilize the orthopedic structure.

At present, the cavity is filled with biomaterial manually using a curet. The curet is handled so as to fill in progressively the existing bone defect. A graft-pusher is used to push the biomaterial in various directions so as to distribute said material better within the cavity. The disposition of the material in the cavity is monitored by using an image intensifier.

Thereafter, the screw is slid on the pin that is subsequently going to advance in the middle of the biomaterial, running the risk of either conflict with the biomaterial (rubbing, breaking up the material, metal particles possibly becoming detached in the screw), or else entraining said material into the head of the femur, which is undesirable. In addition, the length of time needed to fill in the cavity with biomaterial using that technique is about 15 minutes.

It will thus be understood that that technique of delivering biomaterial into the cavity by means of a curet and a graft-pusher presents numerous drawbacks. In particular, it increases the duration of surgery, in particular because of the verifications that need to be performed. Furthermore, it is difficult to ensure that the biomaterial is properly distributed within the cavity.

There therefore exists a real need to have a device for delivering biomaterial into a predetermined portion of a bone that enables the filling of the cavity with the biomaterial to be accelerated and that enables the distribution of the biomaterial within the cavity to be improved.

To achieve this object, the invention provides a device for delivering small spheres of a biomaterial into a determined portion of a bone, the device being characterized in that it comprises:

- a cylindrical hollow body of inside diameter D1 having a filling first end and a second end provided with snap-fastening means;
- a shutter-forming guide rod having a main portion that is cylindrical with an outside diameter D2 and presenting, close to its second end, an enlarged cylindrical portion suitable for co-operating with the snap-fastening means of the body to secure said rod in temporary manner in said body; and
- a piston constituted by a cylindrical part presenting an outside diameter D3 and an axial bore of diameter D4, the diameter D3 being slightly less than the inside diameter D1 of the body and the inside diameter D4 being slightly greater than the diameter D2 of the rod so that after the snap-fastening has been released, said rod can slide inside said piston and in a manner that is proof against the spheres, and the piston can slide in the annular space that exists between said rod and said body and in a manner that is proof against the spheres.

It will be understood that because of the possibility of moving the body of the device relative to the rod, and more precisely relative to its shutter-forming enlarged cylindrical portion, it is possible to locate accurately the zone in which the spheres are to be put into place in the cavity. It will also be understood that because of the action of the piston whose outside diameter is smaller than the diameter of the body and thus of the cavity, it is possible to obtain a good distribution of biomaterial spheres against the wall of the cavity.

In a preferred embodiment, the rod includes an axial bore opening out into its second end that is provided with an enlarged portion, the bore extending over at least a fraction of the length of the rod.

The axial bore of the rod enables the entire device to be guided while it is being inserted into the cavity by means of a pin that has previously been put into place.

Also preferably, said filling first end of the hollow body is extended by a piece having a frustoconically-shaped recess opening out into said axial bore of said body. This flared portion makes it easier to fill the annular space between the body and the rod with spheres, in the manner of a funnel.

Also preferably, said snap-fastening means disposed at the second end of said body comprise longitudinal slots formed in the second end of said body and portions in relief disposed at the second end of said body and projecting into said axial bore, and said enlarged cylindrical portion of the rod includes a substantially cylindrical side face in which a groove is formed suitable for receiving the portions in relief on said body.

Other characteristics and advantages of the invention will appear better on reading the following description of a preferred embodiment of the invention given by way of non-limiting example. The description refers to the accompanying figures, in which:

FIG. 1 is an elevation view of the body of the biomaterial delivery device, seen from above;

FIG. 1A is an end view of the FIG. 1 body;

FIG. 2 is an elevation view of the piston;

FIG. 2A is an end view of the FIG. 2 piston;

FIG. 3 is an elevation view of the rod together with its shutter;

FIG. 3A is an end view of the FIG. 3 rod;

FIG. 4 shows the first stage of using the device which consists in putting the spheres of biomaterial into place;

FIG. 5 shows the following step which consists in putting the piston into place inside the body of the device;

Figure 6:
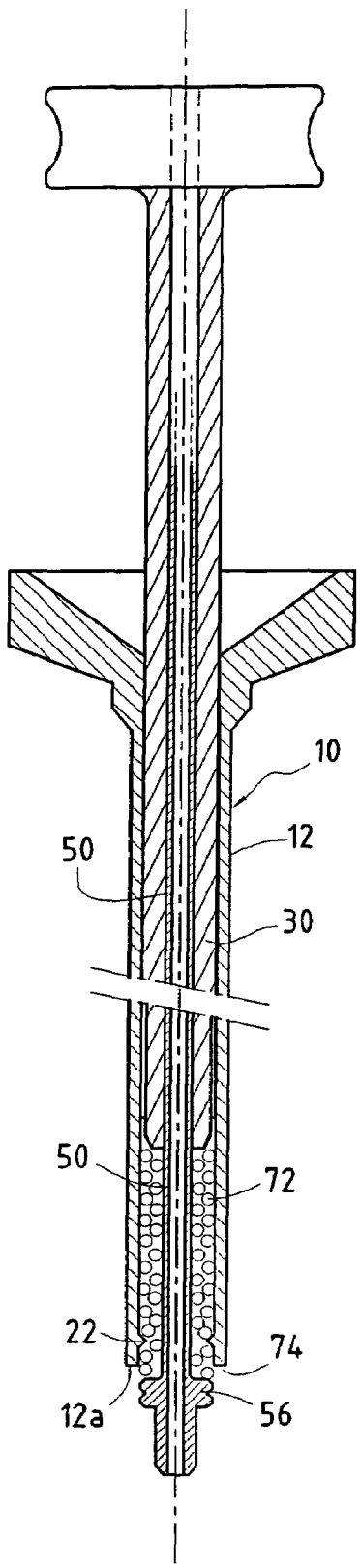
FIG. 6 shows the following step of use in which the body is moved away from the end of the rod to enable biomaterial spheres to escape.
Figure 7:
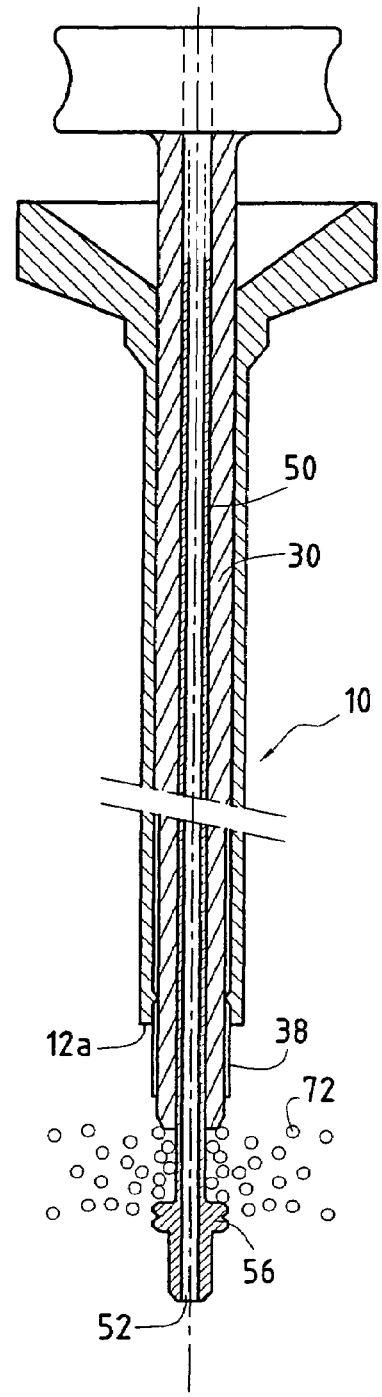
FIG. 7 shows the final state of the device once the piston has expelled all of the spheres into the cavity formed in the bone.

With reference initially to FIGS. 1 to 3, there follows a description of the various parts of the device for delivering spheres of biomaterial.

In FIGS. 1 and 1A, there can be seen the body of the device. The body 10 is constituted by a tubular part 12 that thus presents an axial bore 14 of inside diameter D1. This tubular part presents a first end 16 which is provided with longitudinal slots such as 18, defining between them elastically deformable tongues 20. On their inside faces 20a, the tongues are provided with respective catch-forming portions in relief 22 for use, as explained below, as snap-fastener members. The second end 24 of the body 10 is preferably provided with a flared extension 26 which defines a frusto-conical recess 28 in the form of a funnel opening out into the axial bore 14 of the body 10.

FIGS. 2 and 2A show the second element of the device for delivering spheres of biomaterial, this element constituting the piston 30. It is likewise essentially constituted by a tubular part 32 that therefore presents an axial bore 34. The diameter of the axial bore 34 is referenced D4 while the outside diameter of the piston 30 is equal to D3. The diameter D3 is slightly smaller than the diameter D1 so as to allow the piston to slide in the body while still being "proof" against spheres of biomaterial. At its first end 36, the piston 30 is preferably provided on its outside face with fluting such as 38 extending over a fraction of its length. At its other end 40, the piston 30 is provided with a drive piece 42. The length L3 of the piston 30 is longer than the length L1 of the body 10.

FIGS. 3 and 3A show the rod of the device of the invention. This rod presents a main portion of outside diameter D2 and it is of length L2 perceptibly longer than the lengths L1 and L3 of the body and of the piston. The rod 50 preferably presents an axial bore 52 which extends over at least a fraction of its length and preferably over its entire length. Close to its end 54, the rod has an annularly-shaped portion 56 presenting a diameter D'2 that is perceptibly greater than the diameter D2 of the rod 50. The annular portion 56 preferably presents an annular groove 58 whose function is explained below. The terminal portion 60 of the rod 50 also presents an enlarged diameter but smaller than the diameter D'2 of the enlarged portion 56. The diameter D2 is slightly smaller than the diameter D4 of the axial bore in the piston so as to be "proof" against the spheres of biomaterial.

These various elements constituting the biomaterial delivery device are preferably made of a steel presenting the qualities required for surgical instruments.

With reference now to FIGS. 4 to 7, there follows a description of how the device is used to deliver small spheres of biomaterial into the cavity formed in the portion of bone concerned.

FIG. 4 shows the rod 50 in place inside the body 10 of the device. In this position, the shutter-forming enlarged portion 56 of the rod 50 is snap-fastened to the body 10 of the device by means of the snap-fastening catches 22 co-operating with the groove 58 in the enlarged portion 56. This assembly thus defines an annular volume 70 between the wall of the body 10 and the outside portion of the rod 50, this volume being closed at its bottom end by the shutter 56 of the rod 50. The funnel 28 is used to introduce the required quantity of small spheres of biomaterial 72 into the annular space 70. Thereafter, as shown in FIG. 5, the piston 30 is put into place, the piston having its axial bore 34 engaged on the rod 50. The piston 30 is introduced into the axial bore of the body 10 in such a manner as to cause the spheres of biomaterial 72 to be lightly compressed.

In the following step, shown in part in FIG. 6, the assembled device in the state shown in FIG. 5 is inserted into the cavity made in the bone. The end 60 of the rod constitutes a limit on how far the device can be pushed into the cavity, thereby ensuring that it is properly positioned. In the following step, the body 10 is moved away from the shutter 56 of the rod 50, the rod remaining stationary. This causes the rod to be released relative to the body 10, thereby obtaining an opening 74 between the shutter 56 and the bottom edge 12a of the body 10. This opening 74 enables the spheres of biomaterial 72 to escape from the volume in which they were initially confined. By keeping the body 10 in position and by causing the piston 30 to be pushed in relative thereto, the transfer of the spheres 72 into the inside of the cavity is facilitated. Pushing in the piston also serves to press the spheres 72 against the inside wall. It should be added that by causing the piston 30 to turn about its axis, the fluting 38 formed in its outside face serves to improve the delivery and the distribution of the spheres 72 against the wall of the cavity.

It should also be stated that the axial bore 52 provided in the rod 50 serves to guide the device along the guide pin previously put into place in the cavity.

In a preferred embodiment of the device, the inside diameter D1 of the body is about 13 millimeters (mm). Its length L1 is about 145 mm.

The outside diameter D3 of the piston 30 is about 12.4 mm so as to be less than the inside diameter D1 of the body 10, the axial bore of the piston presenting a diameter of about 5 mm so as to be slightly greater than the outside diameter D2 of the rod 50 which is about 4.4 mm.

Naturally the various diameters D1, D2, D3, and D4 are imposed by the outside diameter of the body 10 of the device, the outside diameter of the body itself being determined by the diameter of the cavity made in the bone, which cavity usually has a diameter of 14 mm.

The invention claimed is:

1. A device for delivering small spheres of a biomaterial into a determined portion of a bone, said device comprising:
   a cylindrical hollow body for containing the spheres to be delivered, and having a proximal end for filling the spheres into the body, and an open distal end provided internally with snap-fastening means through which the spheres are delivered, the cylindrical hollow body having an inner diameter D1 which is substantially constant from the distal end towards the proximal end, and which forms a closed wall between the distal end and the proximal end;
   a shutter-forming guide rod having a proximal end, a distal end, and a main portion that is cylindrical with an outer diameter D2 and presenting, close to the distal end thereof, an enlarged cylindrical portion integral with the main portion and having a diameter substantially equal to the inner diameter D1 of the cylindrical hollow body, the enlarged cylindrical portion being constructed and arranged for releasable engagement with said snap-fastening means of the hollow body to secure said rod in said hollow body, said shutter-forming guide rod being movable between a first position in which the enlarged cylindrical portion is engaged with said snap fastening means, closing thereby the distal end of the hollow body and forming within the hollow body a space for containing the small spheres of biomaterial to be delivered, and a second position in which the enlarged cylindrical portion extends beyond the open distal end of the cylindrical hollow body to open the distal end of the cylindrical hollow body to permit delivery of the spheres; and
   a piston comprising a proximal end, a distal end, and a cylindrical portion presenting an outer diameter D3 and an axial bore of substantially constant diameter D4, the outer diameter D3 being slightly less than the inner diameter D1 of the body, and the diameter D4 being slightly greater than the outer diameter D2 of the guide rod, enabling the piston to slide in an annular space defined between the guide rod and the body, wherein upon release of the engagement of the enlarged cylindrical portion with the snap-fastening means of the hollow body, said rod is slidable within the axial bore of said piston, the guide rod being greater in length than the hollow body or the piston.

2. A device according to claim 1, wherein said rod includes an axial bore opening out into the distal end that is provided with said enlarged portion, the bore of said rod extending over at least a fraction of the length of the rod.

3. A device according to claim 1, wherein said proximal end of said hollow body is extended by a piece having a frustoconically-shaped recess opening into the inner diameter D1.

4. A device according to claim 1, wherein said snap-fastening means disposed in the distal end of said body comprises longitudinal slots formed in the distal end of said body and relief portions disposed at the distal end of said body projecting into the inner diameter D1, said enlarged cylindrical portion of the rod including a substantially cylindrical side face in which a groove is formed for receiving the relief portions.

5. A device according to claim 1, wherein said piston is provided externally with fluting close to the distal end thereof.

* * * * *